(12) United States Patent
Mihashi et al.

(10) Patent No.: US 6,536,900 B2
(45) Date of Patent: Mar. 25, 2003

(54) EYE CHARACTERISTIC MEASURING APPARATUS

(75) Inventors: Toshifumi Mihashi, Tokyo (JP); Yoko Hirohara, Tokyo (JP)

(73) Assignee: Kabushiki Kaisha Topcon (JP)

( * ) Notice: Subject to any disclaimer, the term of this patent is extended or adjusted under 35 U.S.C. 154(b) by 27 days.

(21) Appl. No.: 09/819,354

(22) Filed: Mar. 28, 2001

(65) Prior Publication Data

US 2001/0035939 A1 Nov. 1, 2001

(30) Foreign Application Priority Data

Mar. 28, 2000 (JP) .......................... 2000-089978

(51) Int. Cl.[7] .............................................. A61B 3/10
(52) U.S. Cl. ....................................................... 351/221
(58) Field of Search ................................. 351/204, 205, 351/220, 221; 600/558

(56) References Cited

U.S. PATENT DOCUMENTS

| | | | | | |
|---|---|---|---|---|---|
| 4,789,978 A | * | 12/1988 | Shikama et al. | ....... | 369/112.23 |
| 5,684,779 A | * | 11/1997 | Ohuchida et al. | ....... | 369/112.12 |
| 5,768,001 A | * | 6/1998 | Kelley et al. | ................ | 359/196 |
| 6,199,986 B1 | * | 3/2001 | Williams et al. | ............ | 351/221 |
| 6,299,311 B1 | * | 10/2001 | Williams et al. | ............ | 351/221 |
| 2002/0047992 A1 | * | 4/2002 | Graves et al. | ............... | 351/212 |

* cited by examiner

*Primary Examiner*—Marvin M. Lateef
*Assistant Examiner*—John R. Sanders
(74) *Attorney, Agent, or Firm*—Baker Botts LLP

(57) ABSTRACT

The present invention is intended to provide an eye characteristic measuring apparatus having a projection system for projecting a light source image of small amount onto a fundus of an eye by a reflected light from the fundus, and a wavefront detecting system for detecting a wavefront of luminous flux emitted from the interior of the pupil of the eye by a reflected light from the fundus, where the projection system projects a light source image of small amount onto a fundus of an eye, and the wavefront detection system detects the wavefront of luminous flux emitted from the interior of the fundus by a reflected light from the fundus, and a deflection prism having at least one transmission surface for aberration correction within both optical paths of the projecting system and the wavefront detecting system, can deflect the incident luminous flux.

6 Claims, 6 Drawing Sheets

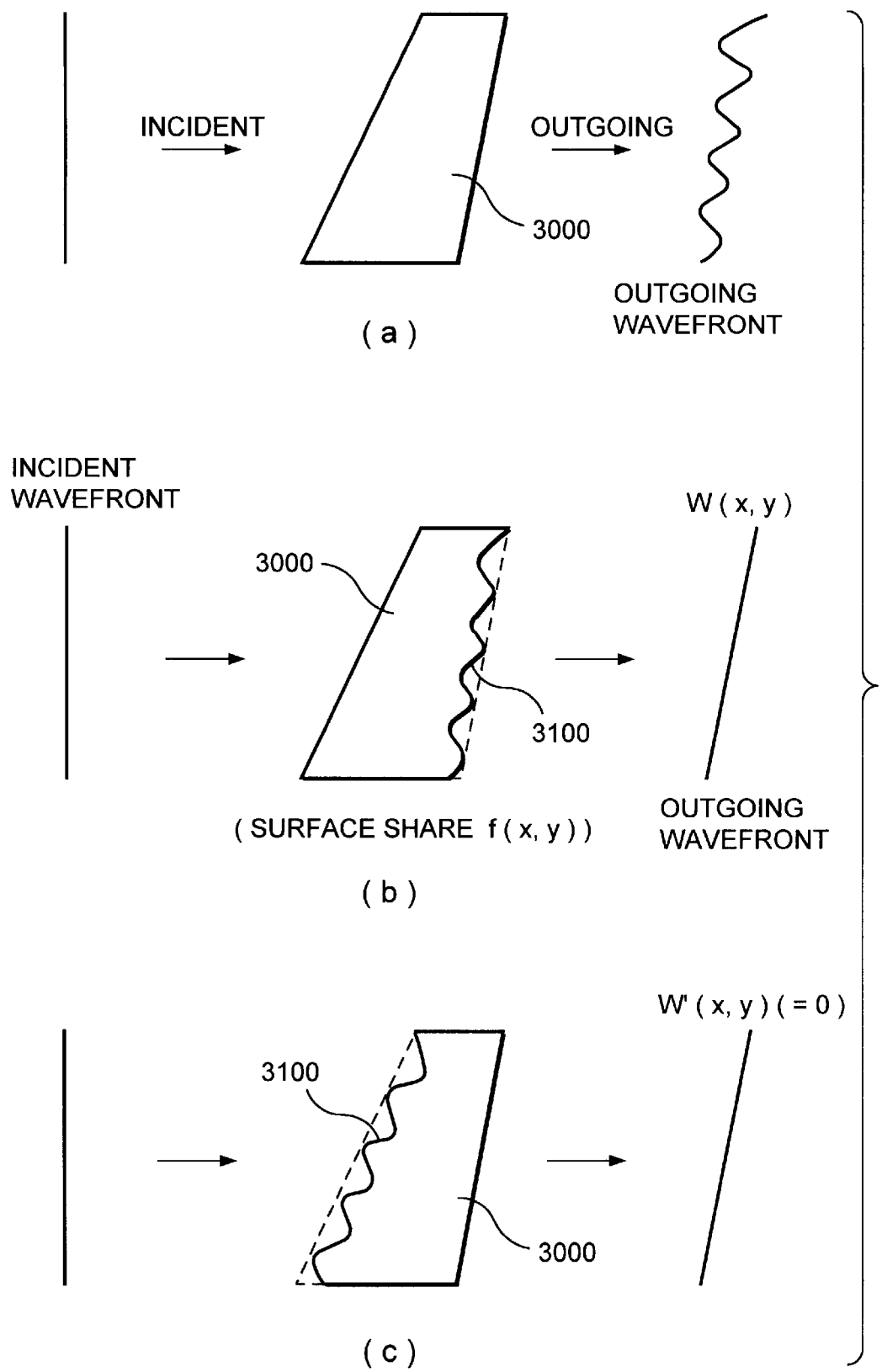
F I G. 3

ZERNIKE POLYNOMIAL COEFFICIENTS

| Number | Order | | Value (waves at 840.0 nm) |
|---|---|---|---|
| | i | j | |
| 1 | 0 | 0 | 0.4433 |
| 2 | 1 | 0 | 0.0000 |
| 3 | | 1 | -0.6638 |
| 4 | 2 | 0 | -0.6919 |
| 5 | | 1 | 0.4687 |
| 6 | | 2 | 0.0000 |
| 7 | 3 | 0 | 0.0000 |
| 8 | | 1 | 0.0000 |
| 9 | | 2 | -0.3405 |
| 10 | | 3 | 0.0090 |
| 11 | 4 | 0 | 0.0000 |
| 12 | | 1 | 0.0091 |
| 13 | | 2 | 0.0212 |
| 14 | | 3 | 0.0000 |
| 15 | | 4 | 0.0000 |
| 16 | 5 | 0 | 0.0000 |
| 17 | | 1 | 0.0000 |
| 18 | | 2 | 0.0000 |
| 19 | | 3 | -0.0056 |
| 20 | | 4 | 0.0001 |
| 21 | | 5 | 0.0000 |
| 22 | 6 | 0 | 0.0000 |
| 23 | | 1 | 0.0000 |
| 24 | | 2 | 0.0002 |
| 25 | | 3 | -0.0041 |
| 26 | | 4 | 0.0000 |
| 27 | | 5 | 0.0000 |
| 28 | | 6 | 0.0000 |

F I G. 4

TRAPEZOID PRISM

TRAPEZOID PRISM   FLAT PLATE

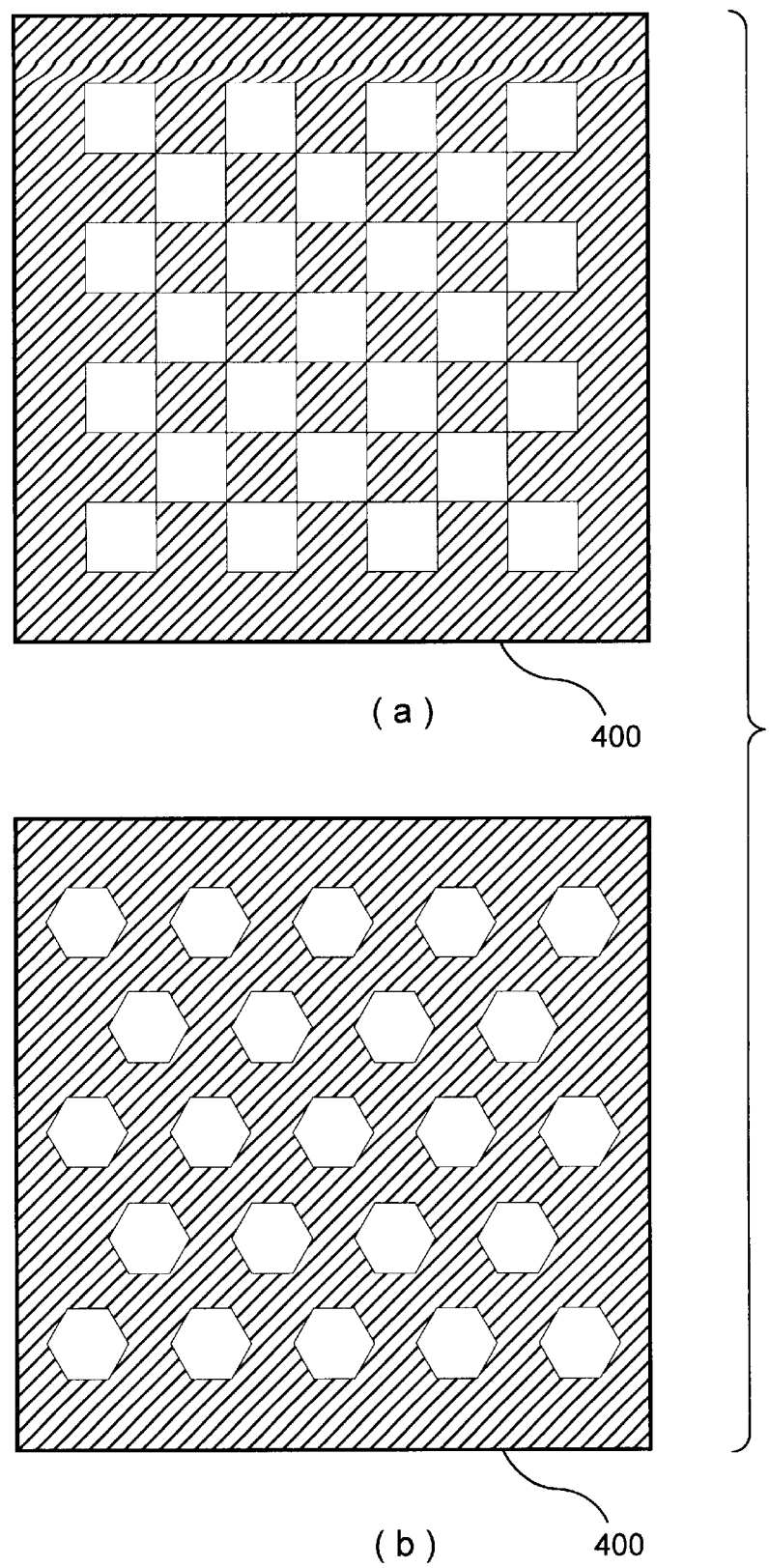
F I G. 7

EYE CHARACTERISTIC MEASURING APPARATUS

BACKGROUND OF THE INVENTION

The present invention relates to an eye characteristic measuring apparatus provided with a projection system for projecting a fine light source image onto a fundus of an eye to be detected and a wavefront detection system for detecting a wavefront of a luminous flux emitted from the inside of a pupil of an eye to be detected by a reflected light from the fundus.

In an eye characteristic measuring apparatus in the prior art, such an apparatus is known that a wavefront of luminous flux is detected where luminous flux from a point source formed on the fundus is transmitted within a pupil of an eye to be detected, and the spherical degree, the astigmatism degree, the astigmatism axis, as well as aberration characteristics of higher order are detected.

In such an eye characteristic measuring apparatus in the prior art, a problem exists in that since a point source is projected onto a fundus, when only a reflected light from one point on the fundus is caught, measurement results of a wavefront are dispersed due to difference of the projection positions affected by a blood vessel on the fundus or the like, and thus the measurement results with high accuracy cannot be obtained.

Therefore it has been proposed that a reflection member for deflecting luminous flux into a common optical path of a projection system and a wavefront detection system is disposed, and while position of a point source image projected onto a fundus is varied, an averaged wavefront from each projection position is detected, and dispersion depending on the projection position is removed, whereby the measurement accuracy is improved.

In the prior art as above described, however, since luminous flux is deflected using a reflection optical element, not only constitution for a reflection surface to be vibrated finely is necessary, but also an optical element to return the optical axis for the reflection optical element is necessary. Thus the optical system is complicated inevitably and also the optical adjustment during assembling is quite difficult.

The present invention intends to solve the problems in the prior art, and is characterized in that a deflection prism to deflect a transmitted luminous flux is used as a deflection optical element, and in order that aberration components such as astigmatism generated in the deflection prism are removed, at least one surface of the deflection prism is made an aberration correction transmission surface such as a aspherical surface.

According to the present invention, since at least one transmission surface of the deflection prism is made an aberration correction surface, the deflection prism can be applied as a deflection member in such an apparatus for the first time, and the present invention is advantageous in that only if the deflection prism arranged within the optical path is rotatable about the optical path simply, the optical axis can be inclined and also the optical system can be made quite simple constitution

SUMMARY OF THE INVENTION

The present invention is a distance measuring apparatus in which a projection system irradiates a measurement luminous flux toward a measurement object, and in a light receiving system, a reflection luminous flux reflected by the measurement object is received by light receiving conversion means, and based on the reflection luminous flux received by the light receiving conversion means, and the distance from the measurement position to the measurement object is measured, wherein an attenuation filter adjusts a light quantity of luminous flux incident to the light receiving conversion means, and deflection means is provided in at least a part of the attenuation filter.

BRIEF DESCRIPTION OF THE DRAWINGS

The accompanying drawings show embodiments of the present invention, in which:

FIG. 3 is a diagram explaining an example of a deflection prism;

FIG. 4 is a diagram showing operation results;

FIG. 7 is a diagram explaining apertures of Hartman plate.

DESCRIPTION OF THE INVENTION

Embodiments of the present invention will be described in connection with the accompanying drawings as follows.

Figure 1:
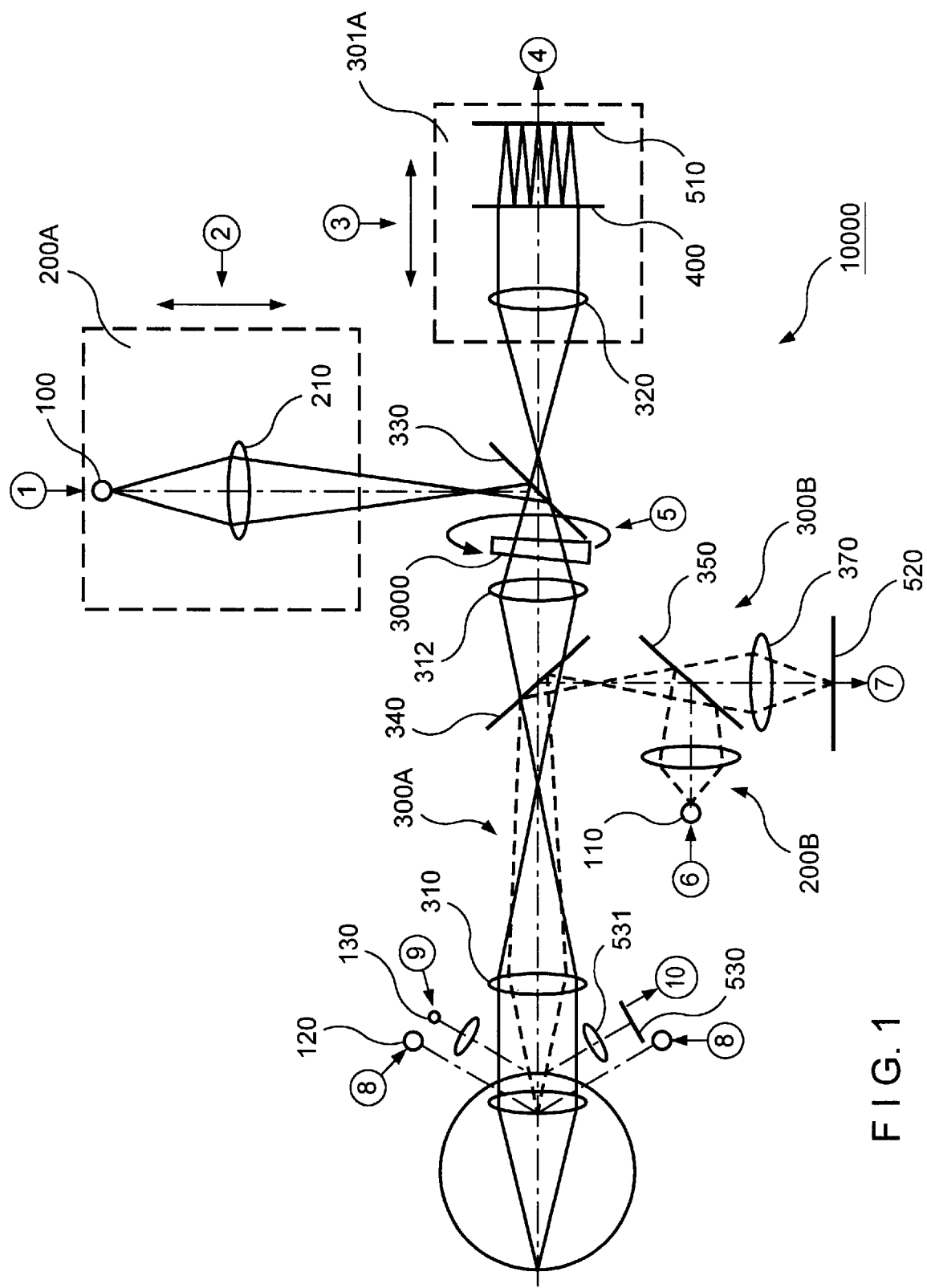
FIG. 1 is a diagram showing a constitution of an eye characteristic measuring apparatus in a first embodiment according to the present invention.

An eye characteristic measuring apparatus 10000 in a first embodiment according to the present invention, as shown in FIG. 1, comprises a first light source 100 that emits luminous flux of a first wavelength, a first illuminating optical system 200A capable of illuminating a small region on a retina of an eye to be detected with luminous flux from the first light source 100 in various illuminating conditions so that illuminating conditions may be varied, a first light receiving optical system 300A where a part of luminous flux reflected and returned from the retina of an eye to be detected is guided to a first light receiving unit 510 through a first transforming member 400 for transforming the reflected luminous flux into at least nine optical beams, a second light receiving optical system 300B where a second luminous flux reflected and returned from the retina of the eye to be detected is guided to a second light receiving unit 520, and an arithmetic unit 600 that determines the optical characteristics of the eye to be detected based on a first signal from the first light receiving unit 510 and corresponding to the inclination angle of the luminous flux. In addition, the first illuminating optical system 200A corresponds to the projection system, and the first light receiving optical system 300A corresponds to the wavefront detecting system Within both optical paths of the first illuminating optical system 200A and the first light receiving optical system 300A, a deflection prism 300 having at least one aberration correction transmission surface and for deflecting incident luminous flux is arranged.

The arithmetic unit 600 controls all the units and systems including a control unit 610. Further the control unit 610 receives signals from the signals ④, ⑦, ⑩ of the first light receiving unit 510, the second light receiving unit 520, a third light receiving unit 530 and controls driving of the first light source 100 to the fourth light source 130 and controls driving of a first driving unit 910 to a third driving unit 930, and also controls a display unit 700 and a memory unit 800.

It is desirable that the first light source 100 emits light having a high spatial coherence and a low temporal coherence. The first light source 100 of the first embodiment is an SLD, and thereby a point source of a high luminance is obtained.

The first light source 100 of the first embodiment does not need necessarily to be an SLD and a laser that emits light having a high spatial coherence may be used by inserting a rotational diffusion plate or the like that lowers the temporal coherence properly.

An SLD that emits light having a low temporal coherence can be used by placing a screen provided with a pinhole at a position corresponding to the light source in the optical path, provided that the SLD has a sufficiently high luminous intensity.

The illuminating light emitted by the first light source 100 may be light of a wavelength in an infrared region, such as 780 nm.

The first illuminating optical system 200A illuminates a small region on the retina of the eye with the luminous flux from the first light source 100. The first illuminating optical system 200A comprises a first collimator lens 210 which illuminates the eye 1000.

The first light receiving optical system 300A receives luminous flux reflected and returned from the retina of the eye and guides the same to the first light receiving unit 510. The first light receiving optical system 300A comprises a first afocal lens 310, a second afocal lens 312, a deflection prism 3000, a first beam splitter 330 and first light receiving means 301A. Also the first light receiving means 301A comprises a first collimate lens 320, a transforming member 400 for converting the reflected luminous flux into at least nine beams and a first light receiving unit 510.

Also, the first beam splitter 330 is inserted in the first light receiving optical system 300A. The first beam splitter 330 sends the light from the first illuminating optical system 200A toward the eye 1000 and transmits the reflected light.

The first light receiving unit 510 receives the light through the first light receiving optical system 300A that transmits the transforming member 400 and generates a first signal ④. In addition, the first light receiving unit 510 corresponds to a photoelectric detector.

The first light source 100 and the fundus of the eye are conjugate to each other, and the fundus of the eye and the light receiving unit 510 are conjugate to each other. Further the transforming member 400 and the pupil of the eye are conjugate to each other, and the pupil of the eye and the surface of the deflection prism 3000 adding the aberration are conjugate to each other.

That is, the front focus of the afocal lens 310 coincides substantially with the anterior segment of the eye as the object to be inspected.

The first illuminating optical system 200A and the first light receiving optical system 300A are disposed in a positional relation in that the luminous flux from the first light source 100 is assumed to be reflected at the focusing point, and relation of making the signal peak in the first light receiving unit 510 by the reflected light maximum is maintained, and the first illuminating optical system 200A and the first light receiving optical system 300A are moved in cooperation in the direction to increase the signal peak in the first light receiving unit 510, and are stopped at the position that the intensity becomes maximum. As a result, the luminous flux from the first light source 100 is focused on the fundus of the eye.

Here the deflection prism 3000 will be described in detail.

The deflection prism 3000 is a wedge shaped-deflection prism made of a light transmission material, and is arranged rotatably about the optical axis in the conjugate position with the pupil of the eye in the common optical path of the eye in the common optical path of the first illuminating optical system 200A and the first light receiving optical system 300A. That is, based on the control signal from the arithmetic unit 600, the third driving unit 930 can rotate the deflection prism 3000.

The deflection prism 3000 is a prism for deflecting the luminous flux from the first light source 100 in a fine angle, and the main light ray of the luminous flux projected onto a fundus of the eye is deflected by a fine angle about the position of the pupil of the eye 1000, and the point source image is formed at the position away from the center by a fine amount on the eye 1000. The luminous flux from the point source is transmitted through the deflection prism 3000 again, and thereby the inclination is returned, and it is projected as the luminous flux of the main light ray in parallel to the optical axis onto the first light receiving unit 510.

Here, if the deflection prism 3000 is rotated at a high speed, the light source image is rotated along the circular locus of the prescribed radius on the fundus of the eye, and an averaged wavefront formed by the luminous flux of the respective point sources on the rotary locus can be detected by the first light receiving unit 510. Therefore the dispersion of the measurement due to difference of the projection position of the point source on the fundus of the eye can be averaged and measured, and the measurement accuracy of the wavefront emitted from the eye 1000 can be greatly improved.

In addition, although the deflection prism 3000 is arranged within the common optical system of the first illuminating optical system 200A (projection system) and the first light receiving optical system 300A (light receiving system), also even if the same deflection prisms 3000 are arranged on the respective optical paths of the first illuminating optical system 200A (projection system) and the light receiving optical system 300A (light receiving system) and both deflection prisms 3000 are synchronized and rotated, similar effect can be obtained.

Next, the transforming member 400 will be described.

The transforming member 400 arranged in the first light receiving optical system 300A is a wavefront transforming unit that converts the reflected luminous flux into a plurality of optical systems, the transforming member 400 employed in the first embodiment comprises a plurality of micro Fresnel lenses arranged in a plane perpendicular to the optical axis.

In order to measure the measurement object in the spherical component and the astigmatism in the third order, the measurement must be performed at least using 17 beams through the measurement object. An example of the transforming member will be shown in FIG. 7(*a*) and FIG. 7(*b*). In any case, the center aperture is arranged in conformity with the optical axis of the optical system.

Here, the micro Fresnel lens will be described in detail.

The micro Fresnel lens is an optical element having annular ridges arranged at a height pitch for a wavelength and having a blaze angle optimum for an outgoing light in parallel to the converging point. The micro Fresnel lens capable of being utilized here is, for example, that having the difference of the optical path length of eight levels applying the semiconductor precise machining technology effectively, and the converging efficiency of 98% can be realized.

The reflected light from the fundus of the eye passes through the second afocal lens 312, the second cylinder lens 320 and the transforming unit 420 and is focused as first order light on the first light receiving unit 510. Here zero-order light corresponds to transmitted luminous flux and the first-order light corresponds to condensed light.

The transforming member 400 may comprise a micro lens unit for performing converging function and an opening unit for performing transmitting function, in each of regions divided in at least seventeen regions.

The transforming member 400 in the first embodiment comprises a wave front transforming member for converting the reflected luminous flux into at least seventeen beams, Next the first light receiving unit 510 receives the plurality of optical beams converted in the transforming member 400. In the first embodiment, the first light receiving unit 510 is CCD that does not generate much read-out noise, the CCD may be of any type of general CCD with low-noise or a cooled CCD for measurement provided with 2000*2000 elements.

An image signal output from a low-noise CCD and its driver can be simply achieved by using an adaptive image input board.

The first light receiving optical system 300A has a substantially conjugate relation with an iris of an eye and the transforming member 400.

A prism 331 is inserted in the first light receiving optical system 300A, and light from the first illuminating optical system 200A is sent to the eye 1000 and the reflected light is transmitted.

Further a working distance adjusting optical system for adjusting a working distance between the eye 1000 being the object and an optical characteristic measuring apparatus 10000, an alignment optical system for adjusting the positional relation of the eye 1000 being the object and the optical characteristic measuring apparatus 10000 in the direction perpendicular to the optical axis, and a second illuminating optical system 200B for illuminating the object are provided.

The alignment is performed as follows. Luminous flux from the second light source 110 of the second illuminating optical system 200B passes through a light converging lens 370, a third beam splitter 350 and the second beam splitter 340, and the eye 1000 being the object is illuminated by luminous flux being substantially in parallel. The reflection luminous flux reflected in the cornea of the eye is emitted in the divergent luminous flux as if it was emitted from the point of ½ of the cornea curvature radius. The divergent luminous flux passes through the third beam splitter 350 being the second light receiving optical system 300B, the second beam splitter 340 and a light converging lens 370, and is received as a spot image in the second light receiving unit 520. When the spot image is deviated from the optical axis on the second light receiving unit 520, the main body of the characteristic measuring apparatus 10000 is moved and adjusted in the vertical direction and the lateral direction so that the spot image comes on the optical axis. When the spot image is coincident with the optical axis on the second light receiving unit 520, the alignment adjustment is completed.

The wavelength of the second light source 110 is different from the wavelength of the first light source 100, and the wavelength larger than this, for example, 940 nm can be selected. In addition, the second light source 110 and the pupil of the eye are conjugate with each other, and the pupil of the eye and the second light receiving unit 520 are conjugate with each other.

The second beam splitter 340 is formed in a dichroic mirror so that the wavelength of the first light source 100 is transmitted and the wavelength of the second light source 110 is reflected, and thereby such state is prevented that the luminous flux in one optical system enters another optical system and noise is produced. When the spot image comes on the optical axis, the alignment adjustment is completed. Also when the front part of the eye is illuminated by the third light source 120, since the image of the eye is formed on the second light receiving unit 520, utilizing the image of the front part of the eye, the alignment adjustment can be performed so that the pupil center is coincident with the optical axis.

Next, the working distance adjustment is performed in that the luminous flux emitted from the fourth light source 130 is irradiated toward the object, and light reflected from the eye being the object is received through the converging lens 531 by the third light receiving unit 530. The third light receiving unit 530 suffices if it can detect variation of the luminous flux position within the surface including the fourth light source 130, the optical axis and the third light receiving unit 530. For example, it can be constituted by the one-dimensional CCD and the position sensing device (PSD) arranged within the surface.

When the eye is at the proper working distance, the spot image from the fourth light source 130 is formed on the optical axis of the third light receiving unit 530, and when the eye is deviated from the proper working distance forward or rearward, the spot image is formed upward or downward from the optical axis.

Figure 2:
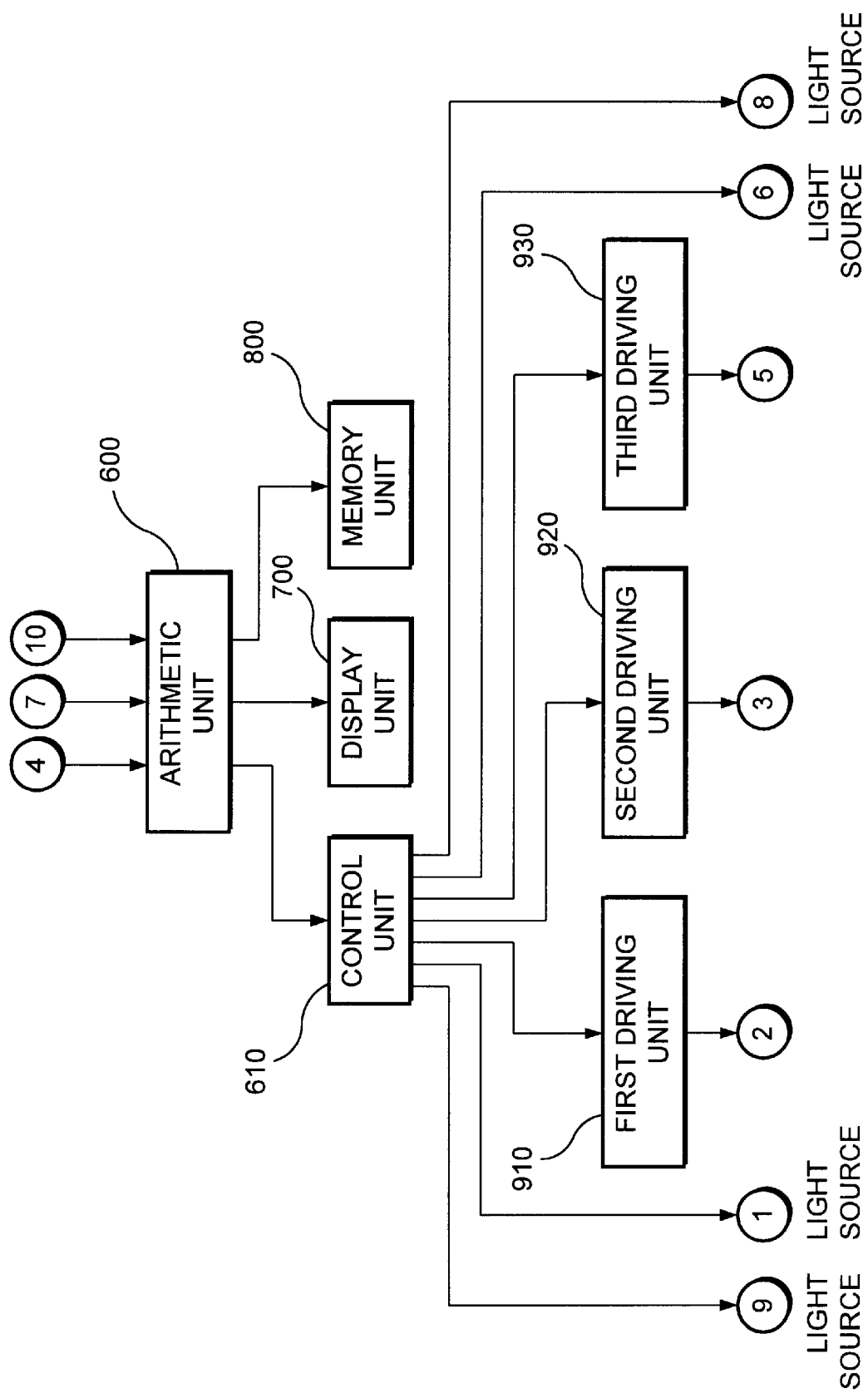
FIG. 2 is a diagram showing an electric constitution of the eye characteristic measuring apparatus.

Here the electric constitution of the eye characteristic measuring apparatus 10000 will be described. based on FIG. 2. The electric constitution of the eye characteristic measuring apparatus 10000 comprises an arithmetic unit 600, a control unit 610, a display unit 700, a memory unit 800, a first driving unit 910, a second driving unit 920 and a third driving unit 930.

The control unit 610 controls the lighting and extinction of the first light source 100 to the fourth light source 130, and controls the first driving unit 910, the second driving unit 920 and the third driving unit 930. based on the control signals from the arithmetic unit 600.

The first driving unit 910 moves the first illuminating optical system 200A as a whole in the optical axis direction according to a signal inputted to the arithmetic unit 600 from the first light receiving unit 510. The first driving unit 910 drives suitable lens moving means so that the illuminating optical system 200A is moved and adjusted. Consequently the first driving unit 910 moves the first illuminating optical system 200A as a whole in the optical axis direction so that the point source is illuminated to the retina of the eye.

The second driving unit 920 moves the first light receiving optical system 300A as a whole in the optical axis direction according to a signal inputted to the arithmetic unit 600 from the first light receiving unit 510. The second driving unit 920 drives suitable lens moving means so that the first light receiving optical system 300A is moved and adjusted.

The third driving unit 930 rotates the deflection prism 3000 according to a control signal from the arithmetic unit 600. For the rotation mechanism of the deflection prism 3000, suitable rotation control means such as a motor is adopted.

The eye characteristic measuring apparatus 10000 constituted as above described, performs the measurement of the refracting power of the eye 1000 in the optical system assembling the deflection prism 3000. Concretely it performs the alignment adjustment of the position of the eye 1000. Next the image data are obtained from the first light receiving unit 510. Based on Expression (4) and Expression (5) as described later, Zernike coefficient is calculated. Further after the Zenrike coefficient is calculated, the estimated S, C, Ax, SA, Coma, . . . and the like are displayed on the display unit 700. Thereby the refraction power or the like of the eye 1000 can be measured at high accuracy.

The principle of operation of the arithmetic unit 600 for determining the optical characteristics of the eye 1000 on the basis of the first signal provided by the first photodetecting device 510 and corresponding to the inclination of light will be explained.

The present invention is intended to measure the wave aberration of the eye.

As shown in FIG. 15, a coordinate system XY is defined by an x-axis and a Y-axis on the transforming device 400 and a coordinate system xy is defined by an x-axis and a y-axis on the first photodetecting device 510. A wavefront W(X, Y) expressed by Expression (3) is determined by Expressions (1) and (2).

$$\frac{\partial W(X, Y)}{\partial X} = \frac{\Delta x}{f} \quad \text{Expression (1)}$$

$$\frac{\partial W(X, Y)}{\partial Y} = \frac{\Delta y}{f} \quad \text{Expression (2)}$$

$$W(X, Y) = \sum_{i=0}^{n} \sum_{j=0}^{i} c_{ij} Z_{ij}(X, Y) \quad \text{Expression (3)}$$

Both sides of Expression (3) are differentiated by X and Y to obtain derivatives, and the derivatives are substituted into the left sides of Expressions (1) and (2) to obtain a polynomial of $C_{ij}$.

$Z_{ij}$ of Expression (3) is called Zernike polynomial expressed by Expressions (4) and (5).

$$Z_{nm} = R_n^{n-2m}(r) \left\{ \begin{matrix} \sin \\ \cos \end{matrix} \right\} (n - 2m)\theta$$

where when n−2m>0, sin is applied and when n−2m≦0, cos is applied.

$$R_n^{n-2m}(r) = \sum_{S=0}^{m} (-1)^S \frac{(n-S)!}{S!(m-S)!(n-m-S)!} r^{n-2S} \quad \text{Expression (4)}$$

$$\text{Expression (5)}$$

Unknowns $C_{ij}$ are determined by reducing the mean square error of Expression (6) to a minimum.

$$S(x) = \sum_{i=1}^{data\ number} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta y_i}{f} \right\}^2 \right] \quad \text{Expression (6)}$$

The $C_{ij}$ thus determined are important optical parameters of the eye.

In Zernike polynomial, symbols indicate the followings.
$Z_{10}$, $Z_{11}$: Prisms
$Z_{21}$: S
$Z_{20}$, $Z_{22}$: C, Ax
$Z_{30}$, $Z_{33}$: Arrow aberration
$Z_{31}$, $Z_{32}$: Third-order coma aberration
$Z_{42}$: Third-order spherical aberration
$Z_{41}$, $Z_{43}$: Astigmatism
$Z_{52}$, $Z_{53}$: Fifth-order coma aberration
$Z_{63}$: Fifth-order spherical aberration
$Z_{84}$: Seventh-order spherical aberration Next, concrete constitution of the deflection prism 3000 will be described.

A deflection prism in general has two transmission surfaces inclined to each other. Even if a wavefront of luminous flux incident to a general deflection prism is a plane wave for example, since the deflection prism has optical aberration of higher order, a problem exists in that luminous flux emitted from the deflection prism does not become a plane wave in inclination. Therefore as in the present application, in the measurement that a wavefront emitted from the eye 1000 is detected, and from the detection results of the eye 1000, characteristics are detected, a problem exists in that aberration generated in the deflection prism badly affects the detection results and the wavefront cannot be detected with high accuracy. Therefore in the deflection prism 3000 in the present invention, in order to correct aberration of higher order, at least one surface of the deflection prism 3000 is formed in a transmission plane for aberration correction. In addition, the transmission plane for aberration correction corresponds to a transmission surface for aberration correction.

As shown in FIG. 3(*a*), assuming that luminous flux of a plane wave is incident to the deflection prism 3000, the wavefront of the luminous flux transmitted through the deflection prism 3000, the wavefront of the luminous flux transmitted through the deflection prism 3000 becomes the wavefront inclined at the prescribed angle, but does not become the complete plane wave due to the aberration. The emitted wavefront is made W (x, y).

When aberration of W (x, y) of the emitted wavefront is shown by Zernike polynomial, in similar manner to the Expression (3) as above described, the aberration can be expressed by following Expression $$W(x, y) = \sum_{i=0}^{n} \sum_{j=0}^{i} c_{ij} Z_{ij}(x, y) \quad \text{Expression (7)}$$

On the other hand, aspherical surface shape of the transmission surface of the deflection prism 3000 f(x, y) will be expressed by Zernike polynomial in following Expression.

$$f(x, y) = \sum_{i=0}^{n} \sum_{j=0}^{i} d_{ij} Z_{ij}(x, y) \quad \text{Expression (8)}$$

where x, y are normalized by incident luminous flux in radius of incident luminous flux in the deflection prism 3000.

In order to correct the aberration generated in the deflection prism 3000, in the wavefront and the surface shape formed by terms other than (i, j)=(1, 0) (1, 1), the surface shape satisfying condition of following Expression may be selected.

$$W(x, y) + f(x, y) \cdot (n-1) = 0 \quad \text{Expression (9)}$$

That is, from Expression (7) and Expression (8)
when i≧2

$$d_{ij} = -(C_{ij}/(n-1)) \ (i=2 \ldots, j=0 \ldots 1) \quad \text{Expression (11)}$$

when i<2

$$d_{ij}=0 (i=0, 1, j=0 \ldots i)$$ Expression (12)

If the surface shape by the above-mentioned expressions is selected, an aberration amount other than inclination term of the wavefront in the deflection prism 3000 can be made zero. As shown in FIG. 3(*b*) and FIG. 3(*c*), the plane wave W (x, y) in inclination without aberration can be obtained where aberration of the wavefront of luminous flux transmitted through the deflection prism 3000 is removed.

Here, the above-mentioned deflection prism 3000 will be shown by concrete design example.

For example, defractive index of the deflection prism 3000 to be used is made 1.735047 (defractive index in the eye characteristic measuring apparatus 10000 in used wavelength 840 nm). The deflection prism is assumed under the condition that plane in the incident side of the deflection prism 3000 is inclined with respect to the optical axis by 8.4 degrees, and the plane at the outgoing side is inclined with respect to the optical axis by ten degrees and the transmission deflection angle becomes 1.174567 degrees.

Concrete calculation of Cij in this condition becomes as shown in FIG. 4.

Here, based on the calculated factor Cij and based on Expression (11) and Expression (12), dij is calculated and the surface form f(x, y) for aberration correction is determined.

The surface 3100 for aberration correction calculated by the calculation may be provided at the incident plane of the deflection prism 3000 as shown in FIG. 3(*b*), or may be provided at the outgoing plane as shown in FIG. 3(*c*).

Figure 5:
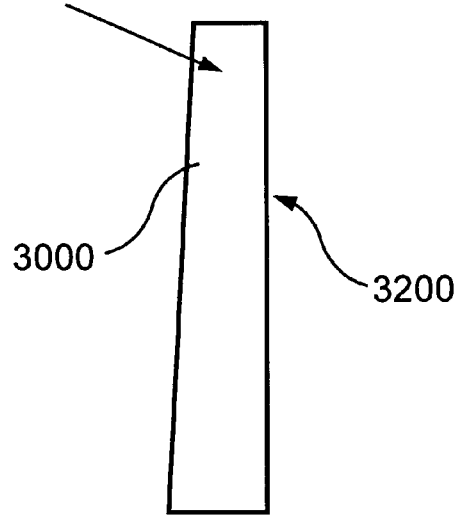
FIG. 5 is a diagram explaining a modification of a deflection prism.

Also as the deflection prism 3000, as shown in FIG. 5, at least one surface of the deflection prism 3000 of wedge shape is not formed in aspherical surface for aberration correction, but may be formed in a diffraction optical element surface 3200 having the same effect.

Figure 6:
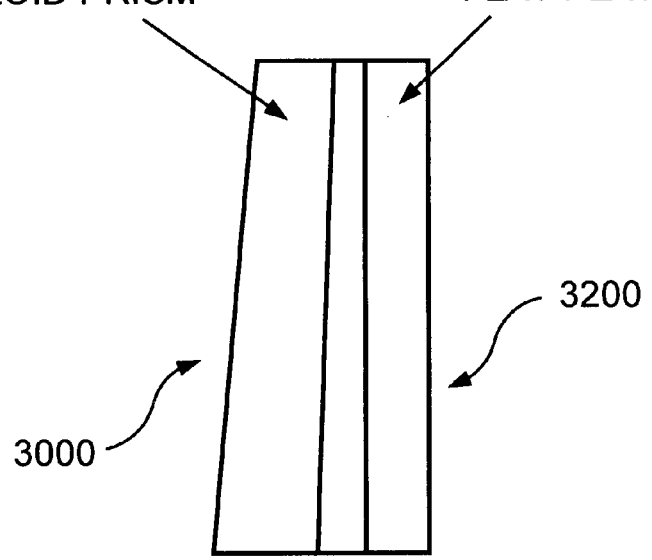
FIG. 6 is a diagram explaining a modification of a deflection prism.

Also as shown in FIG. 6, in order to correct a general deflection prism and to correct only aberration generated in the general deflection prism, the diffraction optical surface 3200 is provided on one plane of the flat plate so that the deflection prism 3000 without aberration may be constituted by two optical members.

In addition, the diffraction optical element surface 3200 corresponds to the transmission surface for aberration correction.

In the present invention as above described, the projection system projects an optical image of small amount onto the fundus of the eye, and the wavefront detection system detects a wavefront of luminous flux emitted from the inside of the pupil of the eye by a reflected light from the fundus of the eye, and the deflection prism having at least one transmission surface for aberration correction provided within both optical paths of the projection system and the wave front detection system can deflect the incident luminous flux. Therefore the present invention has excellent effect that quite accurate measurement can be performed.

What is claimed is:

1. An eye characteristic measuring apparatus comprising:
   a projection system for projecting a light source image of small amount onto a fundus of an eye to be detected;
   a wavefront detection system for detecting a wavefront of luminous flux emitted from the interior of a pupil of the eye by a reflected light from the fundus; and
   a deflection prism having at least one transmission surface for aberration correction within both optical paths of said projection system and said wavefront detection system, said prism deflecting incident luminous flux.

2. The eye characteristic measuring apparatus as set forth in claim 1, wherein said deflection prism is arranged in an optical path commonly used for the projection system and the wavefront detection system, or is arranged in a separate optical path.

3. The eye characteristic measuring apparatus as set forth in claim 2, wherein the deflection prism is rotatable about the optical axis.

4. The eye characteristic measuring apparatus as set forth in claim 1, wherein the transmission surface for aberration correction is a transmission surface of aspherical surface.

5. The eye characteristic measuring apparatus as set forth in claim 1, wherein the transmission surface for aberration correction is a diffraction optical element surface.

6. The eye chracteristic measuring apparatus as set forth in claim 1, said wavefront detection system comprising:
   a Hartman diaphragm having a plurality of aperture irises; and
   a photoelectric detector for detecting an attained position of luminous flux transmitted through each aperture of the Hartman diaphragm.

* * * * *